US007943341B2

(12) United States Patent
Schloesser et al.

(10) Patent No.: US 7,943,341 B2
(45) Date of Patent: May 17, 2011

(54) DNA CONSTRUCT AND PROCESS FOR THE FERMENTATIVE PRODUCTION OF FUSION PROTEINS

(75) Inventors: Thomas Schloesser, Wolfratshausen (DE); Tobias Dassler, Munich (DE); Kerstin Pfeiffer-Schwiesow, Munich (DE)

(73) Assignee: Wacker Chemie AG, Munich (DE)

( * ) Notice: Subject to any disclaimer, the term of this patent is extended or adjusted under 35 U.S.C. 154(b) by 612 days.

(21) Appl. No.: 11/924,019

(22) Filed: Oct. 25, 2007

(65) Prior Publication Data

US 2008/0166764 A1   Jul. 10, 2008

(30) Foreign Application Priority Data

Oct. 25, 2006 (DE) .......................... 10 2006 050 332

(51) Int. Cl.
*C12P 21/04* (2006.01)
*C07H 21/04* (2006.01)
*C12N 1/34* (2006.01)

(52) U.S. Cl. ................. 435/69.1; 435/320.1; 435/252.3; 536/23.1

(58) Field of Classification Search .................. None
See application file for complete search history.

(56) References Cited

U.S. PATENT DOCUMENTS

| 5,919,895 | A | 7/1999 | Schmid et al. | |
| 6,514,730 | B1 * | 2/2003 | Schmid et al. | ............... 435/69.6 |
| 2008/0166764 | A1 | 7/2008 | Schloesser et al. | |

FOREIGN PATENT DOCUMENTS

| EP | 0 338 410 B1 | 9/1994 |
| EP | 0 448 093 B1 | 3/1996 |
| EP | 0 677 109 B1 | 4/2000 |
| EP | 1-364 029 B1 | 12/2005 |
| EP | 1 916 305 B1 | 6/2010 |
| JP | 4-211391 A2 | 8/1992 |
| WO | WO-2006/017929 A1 | 2/2006 |

OTHER PUBLICATIONS

Hagenmaier et al A New Periplasmic Protein of *Escherichia coli* Which is Synthesized in Spheroplasts but not in Intact Cells J. of Bacteriology, Mar. 1997, p. 2073-2076.*
Planson et al., "Assistance of Maltose Binding Protein to the in Vivo Folding of the Disulfide-Rich C-Terminal Fragment from *Plasmodium falciparum* Merozoite Surface Protein 1 Expressed in *Escherichia coli*," Biochemistry 2003, v. 42, pp. 13202-13211.
Georgiou, George et al., "Preparative expression of secreted proteins in bacteria: status report and future prospects," Current Opinion in Biotechnology 2005, v. 16, pp. 538-545.
Cornelis, Pierre, "Expressing genes in different *Escherichia coli* compartments," Current Opinion in Biotechnology, 2000, v. 11, pp. 450-454.
Esposito, Dominic et al., "Enhancement of soluble protein expression through the use of fusion tags," Current Opinion in Biotechnology, 2006, v. 17, pp. 353-358.
European Search Report, 17, Mar. 2008, pp. 1-2.
Patbase abstract corresponding to EP 0 338 410 B1, Sep. 28, 1994.
US 6,514,730 B1 corresponding to EP 0 448 093 B1, Sep. 28, 1994.
Choi et al., Lee et al., Secretory and extracellular production of recombinant proteins using *Escherichia coli*, Appl. Microbiol. Biotechnol., 2004, pp. 625-635, vol. 64.
Tudyka et al., Skerra et al., Protein Science, 1997, pp. 2180-2187, vol. 6.
Jeong et al., Lee et al., Applied and Environmental Microbiology, 2002, vol. 68, pp. 4979-4985, No. 10.
Li et al., Protein Expression and Purification, 2002, pp. 437-447, vol. 25.
Hagenmaier et al., A New Periplasmic Protein of *Escherichia coli* Which is Synthesized in Spheroplasts but Not in Intact Cells, Journal of Bacteriology, 1997, pp. 2073-2076.
Garbe et al., Indole-inducible proteins in bacteria suggest membrane and oxidant toxicity, Arch. Microbiol., 2000, pp. 78-82, vol. 173.
Ray et al., Production of salmon calcitonin by direct expression of a glycine-extended precursor in *Escherichia coli*, Protein Expression and Purification, 2002, pp. 249-259.
Yang et al., Applied and Environmental Microbiology, 1998, pp. 2869-2874, vol. 64, No. 8.
Nagahari et al., The EMBO Journal, 1985, pp. 3589-3592, vol. 4, No. 13A.
Wadensten et al., Biotechnology and Applied Biochemistry, 1991, pp. 412-421, vol. 13.
Gerber et al., Absolute quantification of proteins and phosphoproteins from cell lysates by tandem MS, PNAS, 2003, pp. 6940-6945, vol. 100, No. 12.
Hochleitner et al., The Journal of Biological Chemistry, 2005, pp. 2536-2542, vol. 280, No. 4.
Zhang et al., Extracellular accumulation of recombinant proteins fused to the carrier protein YebF in *Escherichia coli*, Nature Biotechnology, 2006, pp. 100-104.
Raffa et al., Abstracts of the General Meeting of the American Society for Microbiology ASM, 2001, p. 413, Article H-100, vol. 101.
Hagenmaier, S. et al., "A New Periplasmic Protein of *Escherichia coli* Which is Synthesized in Spheroplasts but not in Intact Cells," J. of Bacteriology, Mar. 1997, v. 179, No. 6, p. 2073-2076.

* cited by examiner

*Primary Examiner* — Manjunath N Rao
*Assistant Examiner* — Kagnew H Gebreyesus
(74) *Attorney, Agent, or Firm* — Brooks Kushman P.C.

(57) ABSTRACT

A DNA construct that allows the inexpensive production of a target protein in *E. coli*, consisting of a nucleic acid sequence encoding a signal peptide which is operably linked with a gene coding for a carrier protein which is linked with a gene coding for the target protein via a gene coding for a cleavable sequence S, wherein the gene coding for a carrier protein is the spy gene from *E. coli*.

15 Claims, 6 Drawing Sheets

Fig. 1: Schema: fusion proteins

Fig. 2: Plasmid pKP689

Fig. 3: Plasmid pT1249

Fig. 4: Plasmid pKP700

Fig. 5: Plasmid pEX-spy-IFNa2b

Fig. 6 in each case 5 µl supernatant:
A: WCM105/pKP700
B: WCM105/pT1249
MW: molecular weight standard

SEQUENCE LISTING

<160> NUMBER OF SEQ ID NOS: 24

<210> SEQ ID NO 1
<211> LENGTH: 414
<212> TYPE: DNA
<213> ORGANISM: Escherichia coli
<300> PUBLICATION INFORMATION:
<303> JOURNAL: J. Bacteriol.
<304> VOLUME: 179
<305> ISSUE: 6
<306> PAGES: 2073-2076
<307> DATE: 1997

<400> SEQUENCE: 1

```
gcagacacca ctaccgcagc accggctgac gcgaagccga tgatgcacca caaaggcaag      60
ttcggtccgc atcaggacat gatgttcaaa gacctgaacc tgaccgacgc gcagaaacag     120
cagatccgcg aaatcatgaa aggccagcgt gaccagatga acgtccgcc gctggaagaa     180 cgccgcgcaa tgcatgacat cattgccagc gataccttcg ataaagtaaa agctgaagcg     240
cagatcgcaa aaatggaaga acagcgcaaa gctaacatgc tggcgcacat ggaaacccag     300
aacaaaattt acaacatcct gacgccggaa cagaaaaagc aatttaatgc taattttgag     360
aagcgtctga cagaacgtcc agcggcaaaa ggtaaaatgc ctgcaactgc tgaa           414
```

<210> SEQ ID NO 2
<211> LENGTH: 138
<212> TYPE: PRT
<213> ORGANISM: Escherichia coli
<300> PUBLICATION INFORMATION:
<303> JOURNAL: J. Bacteriol.
<304> VOLUME: 179
<305> ISSUE: 6
<306> PAGES: 2073-2076
<307> DATE: 1997

<400> SEQUENCE: 2

```
Ala Asp Thr Thr Thr Ala Ala Pro Ala Asp Ala Lys Pro Met Met His
1               5                   10                  15

His Lys Gly Lys Phe Gly Pro His Gln Asp Met Met Phe Lys Asp Leu
            20                  25                  30
```

```
Asn Leu Thr Asp Ala Gln Lys Gln Gln Ile Arg Glu Ile Met Lys Gly
         35                  40                  45
Gln Arg Asp Gln Met Lys Arg Pro Pro Leu Glu Glu Arg Ala Met
 50                  55                  60
His Asp Ile Ile Ala Ser Asp Thr Phe Asp Lys Val Lys Ala Glu Ala
 65                  70                  75                  80
Gln Ile Ala Lys Met Glu Glu Gln Arg Lys Ala Asn Met Leu Ala His
                 85                  90                  95
Met Glu Thr Gln Asn Lys Ile Tyr Asn Ile Leu Thr Pro Glu Gln Lys
                100                 105                 110
Lys Gln Phe Asn Ala Asn Phe Glu Lys Arg Leu Thr Glu Arg Pro Ala
            115                 120                 125
Ala Lys Gly Lys Met Pro Ala Thr Ala Glu
        130                 135

<210> SEQ ID NO 3
<211> LENGTH: 69
<212> TYPE: DNA
<213> ORGANISM: Escherichia coli
<300> PUBLICATION INFORMATION:
<303> JOURNAL: J. Bacteriol.
<304> VOLUME: 179
<305> ISSUE: 6
<306> PAGES: 2073-2076
<307> DATE: 1997

<400> SEQUENCE: 3
atgcgtaaat taactgcact gtttgttgcc tctaccctgg ctcttggcgc ggctaacctg    60
gcccatgcc                                                           69

<210> SEQ ID NO 4
<211> LENGTH: 30
<212> TYPE: DNA
<213> ORGANISM: Artificial
<220> FEATURE:
<223> OTHER INFORMATION: oligonucleotides spy fw primer

<400> SEQUENCE: 4
ggaattctga aaggaaggat atagaatatg                                    30

<210> SEQ ID NO 5
<211> LENGTH: 28
<212> TYPE: DNA
<213> ORGANISM: Artificial
<220> FEATURE:
<223> OTHER INFORMATION: oligonucleotide spy-rev primer

<400> SEQUENCE: 5
gctctagatt tacgttagtg gtgatcag                                      28

<210> SEQ ID NO 6
<211> LENGTH: 49
<212> TYPE: DNA
<213> ORGANISM: Artificial
<220> FEATURE:
<223> OTHER INFORMATION: T1 oligonucleotides used to generate peptide
      T1249

<400> SEQUENCE: 6
cgaaatcgaa ggtcgttggc aggaatggga acagaaaatc accgctctg               49

<210> SEQ ID NO 7
<211> LENGTH: 48
<212> TYPE: DNA
```

-continued

```
<213> ORGANISM: Artificial
<220> FEATURE:
<223> OTHER INFORMATION: T2  oligonucleotides used to generatie the
      peptide T1249

<400> SEQUENCE: 7
ctggaacagg ctcagatcca gcaggaaaaa aacgaatacg aactgcag                      48

<210> SEQ ID NO 8
<211> LENGTH: 44
<212> TYPE: DNA
<213> ORGANISM: Artificial
<220> FEATURE:
<223> OTHER INFORMATION: T3  oligonucleotides used to generatie the
      peptide T1249

<400> SEQUENCE: 8
aaactggaca aatgggctag cctgtgggaa tggttctgac tgca                          44

<210> SEQ ID NO 9
<211> LENGTH: 67
<212> TYPE: DNA
<213> ORGANISM: Artificial
<220> FEATURE:
<223> OTHER INFORMATION: T4  oligonucleotides used to generatie the
      peptide T1249

<400> SEQUENCE: 9
gtcagaacca ttcccacagg ctagcccatt tgtccagttt ctgcagttcg tattcgtttt         60
tttcctg                                                                   67

<210> SEQ ID NO 10
<211> LENGTH: 66
<212> TYPE: DNA
<213> ORGANISM: Artificial
<220> FEATURE:
<223> OTHER INFORMATION: T5  oligonucleotides used to generatie the
      peptide T1249

<400> SEQUENCE: 10
ctggatctga gcctgttcca gcagagcggt gattttctgt tcccattcct gccaacgacc         60
ttcgat                                                                    66

<210> SEQ ID NO 11
<211> LENGTH: 52
<212> TYPE: DNA
<213> ORGANISM: Artificial
<220> FEATURE:
<223> OTHER INFORMATION: T6  oligonucleotides used to generatie the
      peptide T1249

<400> SEQUENCE: 11
gatctttttt ccgtccgctt ccgctttcgc ttggcaggaa tgggaacaga aa                 52

<210> SEQ ID NO 12
<211> LENGTH: 50
<212> TYPE: DNA
<213> ORGANISM: Artificial
<220> FEATURE:
<223> OTHER INFORMATION: T7 oligonucleotides used to generatie the
      peptide T1249

<400> SEQUENCE: 12
atcaccgctc tgctggaaca ggctcagatc cagcaggaaa aaaacgaata                    50

<210> SEQ ID NO 13
```

```
<211> LENGTH: 50
<212> TYPE: DNA
<213> ORGANISM: Artificial
<220> FEATURE:
<223> OTHER INFORMATION: T8 oligonucleotides used to generatie the
      peptide T1249

<400> SEQUENCE: 13
cgaactgcag aaactggaca aatgggctag cctgtgggaa tggttctgat          50

<210> SEQ ID NO 14
<211> LENGTH: 76
<212> TYPE: DNA
<213> ORGANISM: Artificial
<220> FEATURE:
<223> OTHER INFORMATION: T9 oligonucleotides used to generatie the
      peptide T1249

<400> SEQUENCE: 14
tctgagcctg ttccagcaga gcggtgattt tctgttccca ttcctgccaa gcgaaagcgg    60
aagcggacgg aaaaaa                                                   76

<210> SEQ ID NO 15
<211> LENGTH: 76
<212> TYPE: DNA
<213> ORGANISM: Artificial
<220> FEATURE:
<223> OTHER INFORMATION: T10 oligonucleotides used to generatie the
      peptide T1249

<400> SEQUENCE: 15
ctagatcaga accattccca caggctagcc catttgtcca gtttctgcag ttcgtattcg    60 ttttttttcct gctgga                                                  76

<210> SEQ ID NO 16
<211> LENGTH: 22
<212> TYPE: DNA
<213> ORGANISM: Artificial
<220> FEATURE:
<223> OTHER INFORMATION: oligonucleotide pJF118-seqfw primer

<400> SEQUENCE: 16
catcggctcg tataatgtgt gg                                       22

<210> SEQ ID NO 17
<211> LENGTH: 44
<212> TYPE: DNA
<213> ORGANISM: Artificial
<220> FEATURE:
<223> OTHER INFORMATION: oligonucleotide spy-T1249fus primer

<400> SEQUENCE: 17
caacgacctt cgatagtact ttcagcagtt gcaggcattt tacc               44

<210> SEQ ID NO 18
<211> LENGTH: 29
<212> TYPE: DNA
<213> ORGANISM: Artificial
<220> FEATURE:
<223> OTHER INFORMATION: oligonucleotide T1249-fus2 primer

<400> SEQUENCE: 18
agtactatcg aaggtcgttg gcaggaatg                                29

<210> SEQ ID NO 19
<211> LENGTH: 33
```

```
<212> TYPE: DNA
<213> ORGANISM: Artificial
<220> FEATURE:
<223> OTHER INFORMATION: oligonucleotide T1249-BfrI primer

<400> SEQUENCE: 19
tagaccgctt aagtcagaac cattcccaca ggc                              33

<210> SEQ ID NO 20
<211> LENGTH: 33
<212> TYPE: DNA
<213> ORGANISM: Artificial
<220> FEATURE:
<223> OTHER INFORMATION: oligonucleotide IFNa2b-fw primer

<400> SEQUENCE: 20
actatcgaag gtcgttgtga cttacctcag acc                              33

<210> SEQ ID NO 21
<211> LENGTH: 32
<212> TYPE: DNA
<213> ORGANISM: Artificial
<220> FEATURE:
<223> OTHER INFORMATION: oligonucleotide IFNa2b-rev primer

<400> SEQUENCE: 21
acctcttaag ctattattct ttggaacgca ag                               32

<210> SEQ ID NO 22
<211> LENGTH: 7
<212> TYPE: PRT
<213> ORGANISM: Artificial
<220> FEATURE:
<223> OTHER INFORMATION: reference peptide  which corresponds to tryptic
      cleavage products of the T1249 peptide

<400> SEQUENCE: 22

Trp Gln Glu Trp Glu Gln Lys
1               5

<210> SEQ ID NO 23
<211> LENGTH: 14
<212> TYPE: PRT
<213> ORGANISM: Artificial
<220> FEATURE:
<223> OTHER INFORMATION: reference peptide  which corresponds to tryptic
      cleavage products of the T1249 peptide

<400> SEQUENCE: 23

Ile Thr Ala Leu Leu Glu Gln Ala Gln Ile Gln Gln Glu Lys
1               5                   10

<210> SEQ ID NO 24
<211> LENGTH: 8
<212> TYPE: PRT
<213> ORGANISM: Artificial
<220> FEATURE:
<223> OTHER INFORMATION: reference peptide  which corresponds to tryptic
      cleavage products of the T1249 peptide

<400> SEQUENCE: 24

Trp Ala Ser Leu Trp Glu Trp Phe
1               5
```

DNA CONSTRUCT AND PROCESS FOR THE FERMENTATIVE PRODUCTION OF FUSION PROTEINS

CROSS-REFERENCE TO RELATED APPLICATIONS

This application claims priority to German Patent Application No. DE 10 2006 050 332.5 filed Oct. 25, 2006 which is herein incorporated by reference.

SEQUENCE LISTING

The text file sequence.txt, created Oct. 24, 2007, and of size 8 kilobytes, filed herewith, is hereby incorporated by reference.

BACKGROUND OF THE INVENTION

1. Field of the Invention

The invention relates to a DNA construct and a process for the fermentative production of fusion proteins using the construct.

2. Background Art

The market for recombinant protein pharmaceuticals ("Biologicals") has grown enormously in recent years. The production costs for protein-based pharmaceutical active substances is still very high thereby providing an impetus for researchers to keep looking for more efficient, and therefore less expensive, processes and systems for their production. Protein producers that can be used include various microorganisms such as bacteria, yeasts, filamentous fungi, or else plant cells or animal cells. However, the Gram-negative enterobacterium *Escherichia coli* (*E. coli*) is currently the most frequently used organism for the production of recombinant proteins, owing to the fact that its genetics and physiology have been studied extensively, it has a short generation time and is simple to handle.

Figure 1:
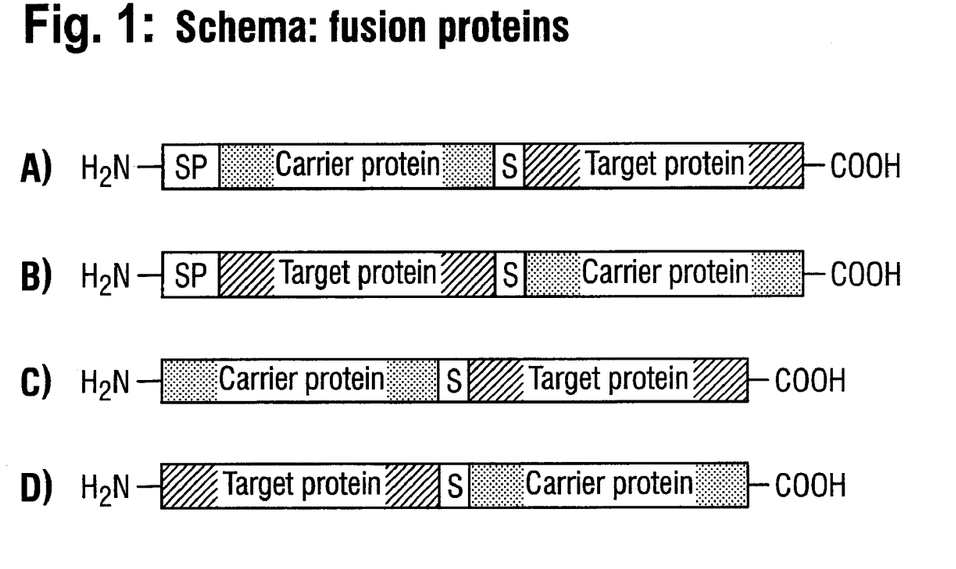

When producing recombinant proteins in *E. coli*, one frequently encounters the problem of inclusion body formation in the cell's cytoplasm. This difficulty can frequently be circumvented by designing the production system in such a way that the cell does not accumulate the recombinant protein to be prepared in each case (also referred to as the target protein as set forth below) in the cytoplasm, but actively secretes it into the periplasm and, ideally, even further into the culture medium. This can be achieved by the cell first synthesizing the target protein as a cytoplasmic precursor fusion protein (FIGS. 1 A and 1 B), the signal peptide (SP) being cleaved off in vivo during the secretion procedure into the periplasm, giving rise to the fusion protein (FIGS. 1 C and 1 D). In *E. coli*, the Sec system is responsible for the transport and the cleavage of the signal peptide. In principle, the extracellular production of target proteins makes use of signal peptides of periplasmic or extracellular proteins of *E. coli*. These *E. coli* proteins are secreted via the Sec pathway. Examples which may be mentioned here are the signal peptides of the *E. coli* proteins PhoA, OmpA, StII, Lpp and MalE.

In accordance with the Sec system, proteins are transported across the cytoplasmic membrane in the unfolded state and subsequently folded in the periplasm. In contrast, the TAT system (Twin Arginine Translocation) allows proteins to be secreted into the periplasm which have already undergone folding in the cytoplasm; however, this requires specific signal peptides (for example signal peptides of the proteins TorA or Tap). The review article by Choi and Lee (2004, Appl. Microbiol. Biotechnol. 64, 625-635) shows the state of the art on the secretory and extracellular production of recombinant proteins with reference to representative examples.

The accumulation of the target protein in the periplasm or in the culture medium has the following advantages over intracellular production: inter alia, 1) the N-terminal amino acid residue of the secreted target protein does not necessarily have to be methionine, but may be identical with the natural starting amino acid of the product,
2) the protease activity in the periplasm is markedly lower than in the cytoplasm,
3) the isolation of a protein from the periplasm or the culture medium is simpler than from the cytoplasm, since the former contain fewer contaminating host proteins, and
4) the formation of any disulfide bridges which may be required is made possible under the oxidative conditions of the periplasm.

In some cases, for example in the secretory production of recombinant proteins or peptides which are particularly sensitive to proteolytic degradation, or which tend to form inclusion bodies, it is necessary or, indeed, imperative for an effective production that the recombinant protein is not coupled directly to a signal peptide, but to the C terminus of a further protein, of the carrier protein (see FIG. 1 A: precursor fusion protein and 1 C: fusion protein). As a part of a secretable fusion protein, it is frequently possible to increase the solubility of the target protein in the fermentation medium. This may be achieved by coupling to a carrier protein followed by the rapid export of the complete precursor fusion protein from the cytoplasm may protect a target protein, or target peptide, which is sensitive to proteolysis from intracellular degradation. In order to protect a sensitive gene product from degradation, and thus to stabilize it, it is also possible to fuse the carrier protein with the C terminus of the target protein (see FIG. 1 B: precursor fusion protein and 1 D: fusion protein). An example for this is the protein glutathione S-transferase, which is used both as carrier protein and as dimerization domain in the secretion of a recombinant protease inhibitor as target protein (Tudyka and Skerra, 1997, Protein Science 6, 2180-2187).

A target protein as used herein means a recombinant protein, protein fragment or peptide that is to be produced extracellularly or periplasmically in yields of greater than 50 mg/l.

A precursor fusion protein as used herein means a protein consisting of a carrier protein and a target protein and a signal peptide (SP). Carrier protein and target protein are linked with one another by a sequence S which is enzymatically or chemically cleavable. The signal peptide is required for the translocation of the fusion protein across the cytoplasmic membrane. This signal peptide is cleaved from the fusion protein during the secretion process into the periplasm, giving rise to the fusion protein.

A fusion protein as used herein means a protein consisting of a carrier protein and a target protein. Carrier protein and target protein are linked with one another via a sequence S which is enzymatically or chemically cleavable.

A carrier protein as used herein means the portion of a precursor fusion protein, or of a fusion protein, which is used for stabilizing the target protein.

After the signal peptide has been cleaved from the precursor fusion protein, the fusion protein is accumulated in the periplasm or in the culture medium. The target protein is preferably linked to the carrier protein via an amino acid sequence, the cleavable sequence S (see FIG. 1), where the target protein can be cleaved off in vitro, either enzymatically or chemically, in a subsequent step, thereby being released.

A carrier protein that has been described as fusion partner for the extracellular production of proteins is, for example, the *E. coli* protein YebF (Zhang et al., 2006, Nature Biotechnology 24, 100-104 and WO2006017929A1).

The YebF protein has a primary structure of 118 amino acids and a molecular weight of 10.8 kDa and is currently the smallest carrier protein described for the heterologous expression of proteins in *E. coli*. A disadvantage in the use of the YebF protein as carrier protein is that the protein contains a total of three cysteine residues, two of which are located in the mature portion of the protein. These two cysteine residues can then form disulfide bridges with the target protein in the oxidizing medium of the periplasm, which may result in a misfolding of the target protein. In the most adverse case, this leads to an unusable target protein. The formation of incorrect disulfide bridges is possible both before and after the target protein has been cleaved from the YebF protein.

Another carrier protein is the OmpF protein of *E. coli*. Jeong and Lee describe the extracellular production of an OmpF-β-endorphin fusion protein with a derivative of the *E. coli* strain BL21 (DE3) (2002, Appl. Environ. Microbiol. 68, 4979-85). With a primary structure of 362 amino acids and a resulting molecular weight of 36 kDa, the OmpF carrier protein is considerably larger and heavier than the YebF carrier protein. This means that an *E. coli* cell, when producing a target protein, is metabolically much more stressed when OmpF is used as the carrier protein instead of YebF. This is particularly clear from the above paper by Jeong and Lee: a production of 5.6 g/l fusion protein only leads to 0.33 g/l β-endorphin.

Another carrier protein is the C-terminal fragment of the HlyA protein of *E. coli*. The hemolysin (HlyA protein) from *E. coli* is a pore-forming exotoxin with a molecular weight of 110 kDa, which is found in pathogenic *E. coli* strains causing, for example, infections of the urinary tract. The HlyA protein is transported out of the cell via the inner and the outer membranes via its own hemolysin transport system. The C-terminal domain of 218 amino acids of the protein, with a molecular weight of 23 kDa, is employed to produce the fusion proteins. This domain is required for the translocation across the two membranes. Human interleukin-6 can be produced extracellularly in the culture supernatant with the aid of an HlyA carrier protein. At 70 μg/l, the yields are extremely low however (Li et al., 2002, Gene 25, 437-447). This fragment, however, is unsuitable for the production of pharmaceutically active proteins, being the fragment of a toxic *E. coli* protein.

A further carrier protein for the extracellular production of target proteins is the eukaryotic protein hirudin from *Hirodo medicinalis*. Hirudin is a thrombin inhibitor, it binds to the protease thrombin with extremely high affinity (Ki=20 fM). The peptide, which consists of 65 amino acids, forms 3 internal disulfide bridges with its 6 cysteine residues. For the extracellular production of target proteins in *E. coli*, the carrier protein hirudin is fused with a bacterial signal peptide. Signal peptides used are, for example, sequences of the *E. coli* proteins PhoA or OmpC (EP1364029B1), or else the signal peptide of the cyclodextrin glycosyltransferase (EP0448093B1). Owing to its biological activity as thrombin inhibitor, hirudin is unsuitable for the production of pharmacological proteins since it must be ensured during the production process of a target protein that no contamination with the carrier protein hirudin is present. This makes the purification process of the target protein very complicated and therefore expensive.

SUMMARY OF THE INVENTION

It is an object of the present invention to provide a DNA construct that makes possible an inexpensive production of a target protein in *E. coli* while avoiding the above-described shortcomings of the prior art. This object is achieved by a DNA construct consisting of a nucleic acid sequence encoding a signal peptide which is operably linked with a gene coding for a carrier protein which is linked with a gene coding for the target protein via a gene coding for a cleavable sequence S, wherein the gene coding for a carrier protein is the spy gene from *E. coli*.

BRIEF DESCRIPTION OF THE DRAWINGS

FIG. 1 shows schematic representations of
A) a precursor fusion protein, consisting of a signal peptide (SP) and a carrier protein, to which the recombinant target protein is coupled via a chemically or enzymatically cleavable sequence (S);
B) a precursor fusion protein consisting of a signal peptide (SP) and a recombinant target protein, to which a carrier protein is coupled via a chemically or enzymatically cleavable sequence (S);
C) a fusion protein consisting of a carrier protein to which the recombinant target protein is coupled via a chemically or enzymatically cleavable sequence (S); and
D) a fusion protein consisting of a recombinant target protein to which a carrier protein is coupled via a chemically or enzymatically cleavable sequence (S).

DETAILED DESCRIPTION OF THE PREFERRED EMBODIMENT(S)

An embodiment of the present invention provides a DNA construct consisting of a nucleic acid sequence encoding a signal peptide which is operably linked with a gene coding for a carrier protein which is linked with a gene coding for the target protein via a gene coding for a cleavable sequence S, wherein the gene coding for a carrier protein is the spy gene from *E. coli*. The spy gene is characterized by SEQ ID NO: 1 or the analogous sequences which are the result of the degeneracy of the genetic code and which code for the Spy protein.

The Spy protein is a periplasmic protein set forth in SEQ ID NO: 2. This sequence corresponds to the mature Spy protein as it is present after secretion into the periplasm and after its signal sequence has been cleaved off. The formation of the Spy protein is induced in the production of spheroplasts (Hagenmaier et al., J. Bacteriol. 179, 2073-2076). Treatment of *E. coli* cells with indole also induces the formation of Spy protein (Garbe et al., 2000, Arch. Microbiol. 173, 78-82). In comparison with the carrier proteins of the prior art, the Spy protein has the following advantages as carrier protein:
a) it is a small extracellular *E. coli* protein;
b) it has no cysteine residues;
c) it is derived from a nonpathogenic *E. coli* strain;
d) it is a carrier protein from a prokaryotic organism without activity in a eukaryotic organism; and
e) it makes possible the inexpensive production, in the culture supernatant, of a recombinant target protein in high yields while maintaining its activity.

The nucleic acid sequence of the signal peptide is preferably a sequence coding for a signal peptide and which has proven itself for the extracellular production of recombinant proteins. Preferably, it takes the form of the signal-peptideencoding nucleic acid sequences of the *E. coli* genes ompA, phoA, ompT, lpp, phoE, ompF, lamB, ompc and malE and of the signal-peptide-encoding nucleic acid sequence of the spy gene from *E. coli* (SEQ ID NO: 3). The signal-peptide-encoding nucleic acid sequence of the spy gene from *E. coli* is more preferred.

The target-protein-encoding nucleic acid sequence codes for a recombinant protein, protein fragment or peptide. Preferably, the nucleic acid sequence codes for a target protein selected from the group consisting of interferons, interleukins, interleukin receptors, interleukin receptor antagonists, granulocyte-colony-stimulating factors, granulocyte-macrophage-colony-stimulating factors, macrophage-colony-stimulating factors, erythropoietin, thrombopoietin, leukemia inhibitors, stem-cell growth factors, tumor necrosis factors, growth hormones, proinsulin, insulin-like growth factors, fibroblast growth factors, platelet-derived growth factors, transforming growth factors, hepatocyte growth factors, bone-morphogenetic factors, nerve growth factors, CNTF (ciliary neurotrophic factor), brain-derived neurotrophic factors (BDNF), glia-cell-line-derived neurotrophic factors, neurotrophin, angiogenesis inhibitors, prourokinase, tissue plasminogen activators, blood clotting factors, protein C, glucocerebrosidase, superoxide dismutase, renin, lysozyme, P450, prochymosin, trypsin inhibitors, elastase inhibitors, lipocortin, reptin, immunoglobulins, single-chain antibodies, complement components, serum albumin, hypoxia-inducing stress proteins, protein kinases, proto-oncogen products, transcription factors, streptokinase, tenecteplase, and virus-constitutive proteins. The nucleic acid sequence more preferably codes for a target protein selected from the group consisting of the interferons and peptides.

The cleavable sequence S for the covalent linking of carrier and target protein preferably takes the form of a nucleic acid sequence which makes possible the enzymatic cleavage of target and carrier protein in the translated fusion protein. Suitable sequences which make possible the cleavage of the fusion protein either chemically (for example by bromocyanin, hydroxylamine, N-bromosuccinimide or acidic hydrolysis) or enzymatically by specific proteases (for example factor Xa, enterokinase, furin, igase, serin endoproteinase Kex, genenase I or PreScission™ protease, which are known in the prior art.

A nucleic acid sequence which makes possible, in the translated fusion protein, the enzymatic cleavage of the target protein, preferably by proteases is more preferred. Most preferably, this takes the form of a nucleic acid sequence which makes possible, in the translated fusion protein, the cleavage of the target protein by means of the eukaryotic protease factor Xa.

In order to generate the DNA construct according to the invention, the nucleic acid sequences coding for the Spy protein, the target protein, the signal peptide and the cleavable sequence S for liberating the target protein are cloned into the plasmid in any sequence over time. The orientation of target protein and Spy protein can be varied as shown in FIGS. 1 A and 1 B. The spy gene is cloned, for example, by the specific amplification by means of the polymerase chain reaction (PCR) using specific oligonucleotides which can be derived from SEQ ID NO: 1, where the resulting PCR fragments can be introduced into a plasmid as the result of a directed ligation.

Useful plasmids include all available DNA molecules that are accessible to genetic engineering, that are replicated extrachromosomally in microorganisms and that comprise a selection marker. For example, it is possible to employ plasmids with a high cellular copy number in *E. coli* (for example plasmids from the pUC series, plasmids from the pQE series, plasmids from the pBluescript series), plasmids with a medium copy number in *E. coli* (for example plasmids of the pBR series, plasmids of the pACYC series) or plasmids with a low copy number in *E. coli* (for example pSC101 or pBeloBAC11). Plasmids with a high cellular copy number in *E. coli* are preferably used. It is preferred to employ a plasmid which already comprises elements for producing a fusion protein, such as, for example, a nucleic acid sequence coding for a signal peptide, and a cleavable sequence S, which makes possible the separation of carrier and target protein. If these elements for the production of a fusion protein are not yet present on the plasmid, they are introduced into the plasmid, by means of cloning techniques known to the skilled worker, in such a way that the individual elements are operably linked with one another.

Subsequently, the constructs of the invention can be excised from the plasmid, for example by means of suitable restriction endonucleases. Preferably, however, the plasmid comprising the DNA construct according to the invention is employed for the transformation of a microorganism. Accordingly, the invention also relates to a plasmid comprising the DNA construct.

The plasmids according to the invention are introduced into the cells of a microorganism strain by a transformation method such as, for example, electroporation or the heat shock method. Plasmid-bearing clones are subsequently selected. The selection takes place via the selection marker located on the plasmid, which confers a resistance to a specific antibiotic. It is preferred to use selection markers which confer resistance to ampicillin or tetracyclin. It is more preferred to employ a selection marker which confers resistance to tetracyclin.

As an alternative to cloning in a plasmid, the DNA construct according to the invention may also be integrated into the chromosome of the microorganism strain used for producing the recombinant target protein. Integration methods that are employed are preferably the systems with temperent bacteriophages, integrative plasmids or integration via homologous recombination, which are known to those skilled in the art.

The invention therefore also relates to a method of producing a fusion-protein-secreting microorganism strain, wherein a DNA construct according to the invention is introduced into a microorganism strain from the family Enterobacteriaceae. The DNA construct according to the invention is preferably employed in the form of a plasmid according to the invention.

It is preferred to use strains of the genus *Escherichia coli* (for example *E. coli* W3110 ATCC 27325). It is more preferred to employ, for the extracellular production of recombinant fusion proteins, *E. coli* strains whose secretion performance of recombinant fusion proteins is improved by at least a factor of 2 in comparison with *E. coli* W3110.

The following *E. coli* strains are examples of preferred strains:
a) BLR: Ray et al. 2002; commercially available via Novagen (Merck Biosciences GmbH, 65796 Bad Soden, Germany);
b) K802=CGSC 5610; Yang et al., 1998; commercially available via the *E. coli* Genetic Stock Center CGSC (830 Kline Biology Tower, MCD Biology Department, 266 Whitney Ave., PO box 208103, Yale University, New Haven, USA);
c) WCM105: obtainable as described in EP0338410B1;
d) MM28=CGSC 5892; Nagahari et al., 1985; commercially available via the *E. coli* Genetic Stock Center CGSC (830 Kline Biology Tower, MCD Biology Department, 266 Whitney Ave., PO box 208103, Yale University, New Haven, USA);

e) RV308=ATCC 31608; EP0677109B1; commercially available via LGC Promochem (Mercatorstr. 51, 46485 Wesel, Germany);
f) RR1: ATCC 31434; Nagahari et al., 1985; commercially available via LGC Promochem (Mercatorstr. 51, 46485 Wesel, Germany); and
g) KG1005 ompT: obtainable as described by Wadensten et al., 1991.

The invention also relates to microorganism strains generated by the methods of the invention. These strains comprise a DNA construct according to the invention or a plasmid according to the invention.

The microorganism strains according to the invention make possible the extracellular production of a fusion protein consisting of the Spy protein, a target protein and a cleavable sequence (S). Accordingly, the invention also relates to fusion proteins consisting of the Spy protein, a target protein and a cleavable sequence (S).

For the purposes of the present invention, extracellular production is taken to mean the accumulation of the recombinant fusion protein of $\geq 50$ mg/l outside the cytoplasm of the microorganism cell. Preferably, this takes the form of the accumulation of the recombinant fusion protein of $\geq 50$ mg/l in the culture medium.

The invention therefore also relates to a process for the fermentative production of a fusion protein by means of a microorganism strain. In accordance with this process, a microorganism strain according to the invention is cultured in a fermentation medium, during which process the fusion protein according to the invention is produced, and, after the fermentation, the fermentation medium is separated from the cells of the microorganism strain.

The fusion protein can be isolated from the periplasm, or the culture medium, by known methods such as centrifugation of the medium in order to remove the cells, if appropriate disruption of the cells, filtration, followed by chromatographic purification, complexing or precipitation of the protein.

Preferred processes include processes in which, after the fermentation medium has been separated off, the target protein is isolated from the periplasm of the cells, the carrier protein first being separated chemically or enzymatically from the target protein and the target protein is subsequently purified. More preferably, the processes as such that, after the fermentation medium has been separated off, the target protein can be isolated from the fermentation medium. Here, the carrier protein is first separated chemically or enzymatically from the target protein, as has already been mentioned. Thereafter, the target protein may be purified by the known methods.

The process according to the invention for producing a fusion protein provide an inexpensive and efficient production of a fusion protein in the culture supernatant.

The fermentation of the bacterial strain for the inventive production of fusion proteins preferably takes place in a complete medium or minimal salt medium. These media are known from the literature.

Carbon sources which can be employed include, in principle, all utilizable sugars, sugar alcohols, organic acids or their salts, starch hydrolyzates, molasses or other substances. It is preferred to employ glucose or glycerol. A combined feeding of several different carbon sources is also possible. Nitrogen sources that may be used are urea, ammonia and its salts, nitrate salts and other N sources. Possible nitrogen sources also include complex amino acid mixtures such as yeast extract, peptone, malt extract, soybean peptone, casamino acids, corn steep liquor and NZ amines (for example Kerry Bio-Science, Chicago, USA). Moreover, further components that improve cell growth may be added to the medium, such as vitamins, salts, yeast extract, amino acids and trace elements.

The strain is preferably incubated under aerobic culture conditions over a period of 16 to 150 hours within a growth temperature range that is best for the strain in question. The preferred temperature range is 15 to 55° C. More preferably, the temperature range is 30 and 37° C. The strain can be grown in shake flasks or in a fermentor, with no limitations regarding volume applying. Growing may take the form of a batch process, a fed-batch process or a continuous process.

The invention furthermore relates to the use of the Spy protein from *E. coli* as carrier protein in the expression of a target protein in *E. coli*.

Utilization of the Spy protein as carrier protein has the following advantages over the use of the known carrier proteins:
a) the fusion proteins are stabilized;
b) misfolding of the target protein is prevented; and
c) high extracellular yields of the target protein are made possible.

The following examples are intended to illustrate the invention in greater detail.

Example 1

Construction of Plasmid pKP689 a) Amplification of the Spy Gene

The spy gene from *E. coli* was amplified by means of the polymerase chain reaction (PCR) using the Taq DNA polymerase (Roche, Mannheim) and proceeding in the customary manner, which is known to the skilled worker. The template used was the chromosomal DNA of the *E. coli* wild-type strain W3110 (ATCC 27325). The primers used were the oligonucleotides spy-fw (SEQ ID NO: 4) with the sequence 5'-GGA ATT CTG AAA GGA AGG ATA TAG AAT ATG-3' and spy-rev (SEQ ID NO: 5) with the sequence 5'-GCT CTA GAT TTA CGT TAG TGG TGA TCA G-3'.

The DNA fragment obtained in the PCR, which is approximately 651 base pairs in length, was subsequently purified by means of a DNA adsorption column from the QIAprep Spin Miniprep Kit (Qiagen, Hilden) following the manufacturer's instructions.

b) Cloning of the spy gene into the plasmid vector pEX2200

Two cleavage sites for the restriction endonucleases EcoRI and XbaI were introduced into the PCR fragment via the primers spy-fw and spy-rev. The purified PCR fragment was cut with the restriction endonucleases EcoRI (Roche, Mannheim) and XbaI (Roche, Mannheim) under the conditions specified by the manufacturer, separated via an agarose gel and then isolated from the agarose gel by means of the QIAquick Gel Extraction Kit (Qiagen, Hilden) following the manufacturer's instructions.

To clone the spy gene, the vector pEX2200 was cut with the restriction endonucleases EcoRI and XbaI under the conditions specified by the manufacturer (Roche, Mannheim). The plasmid was subsequently dephosphorylated at the 5' ends by treatment with alkaline phosphatase (Roche, Mannheim) and then purified by means of QIAquick Gel Extraction Kit (Qiagen, Hilden) as in the case of the PCR fragment. Ligation of the PCR fragment with the cut and dephosphorylated vector was accomplished following the manufacturer's instructions using the T4 DNA ligase (Roche, Mannheim). The transformation of *E. coli* cells of strain W3110 (ATCC 27325) with the ligation mixture was accomplished by means of electroporation in a manner known to the skilled worker. The transformation mixture was applied to LB/tetracyclin agar plates (10 g/l tryptone, 5 g/l yeast extract, 5 g/l NaCl, 15 g/l agar, 20 mg/l tetracyclin) and incubated overnight at 37° C.

Figure 2:
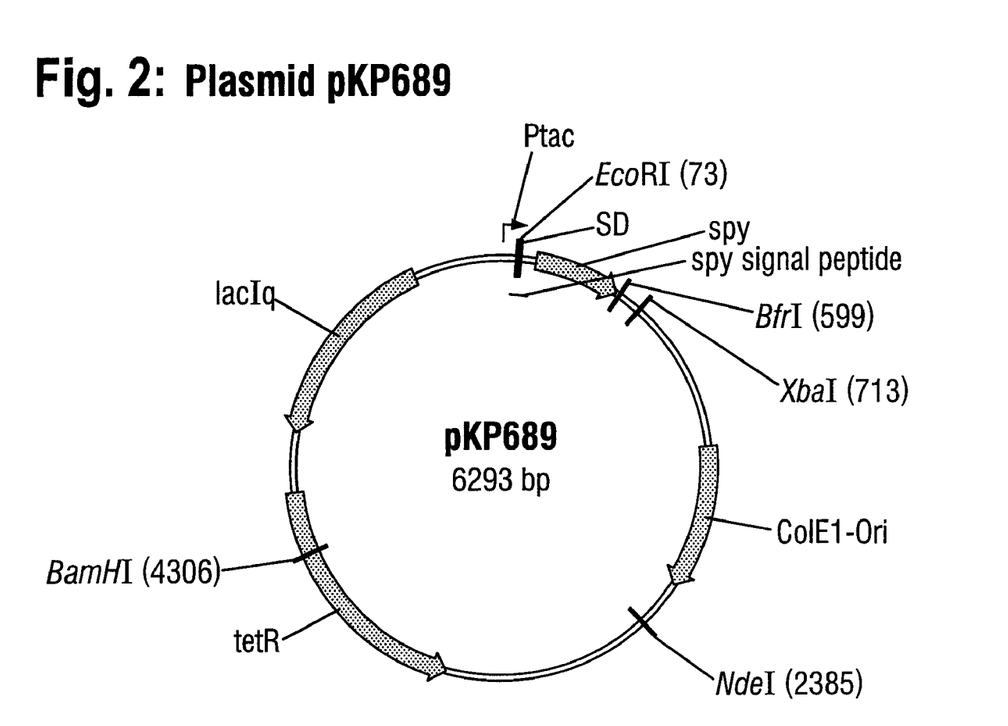
FIG. 2 shows plasmid pKP689

After the plasmids were isolated by means of a QIAprep Spin Miniprep Kit (Qiagen, Hilden), the desired transformants were identified by restriction analysis, and the absence of errors was verified by sequence analysis. In the plasmid pKP689 (FIG. 2) that has been obtained in this manner, the spy gene is under the control of the inducible tac promoter. Plasmid pKP689, which was used for carrying out the other examples, was deposited on 26.06.2006 at the DSMZ (Deutsche Sammlung für Mikroorganismen and Zellkulturen GmbH, D-38142 Brunswick) in compliance with the provisions of the Budapest Treaty as DSM number 18381.

Peptide T1249 is a fusion inhibitor, which prevents the fusion of HIV with the host cell membrane. The peptide, in its active form, is aminated at the C-terminal end and acetylated at the N-terminal end. The production of the unmodified T1249 peptide is described in examples 2 to 6.

Example 2

Cloning of T1249 a) Preparation of Vector pCMT203

To clone the T1249 DNA, the plasmid vector pCMT203 (obtainable as described in EP0448093B1, example 6) was cut with the restriction endonucleases SfuI and PstI under the conditions indicated by the manufacturer (Roche, Mannheim). The plasmid was subsequently dephosphorylated at the 5' ends by treatment with alkaline phosphatase (Roche, Mannheim) and then purified by means of QIAquick Gel Extraction Kit (Qiagen, Hilden), as in the case of the PCR fragment.

b) Phosphorylation of T1249 DNA Fragments

The nucleic acid sequence for the peptide T1249 was generated synthetically with the aid of oligonucleotides. The oligonucleotides T1 (SEQ ID NO: 6), T2 (SEQ ID NO: 7), T3 (SEQ ID NO: 8), T4 (SEQ ID NO: 9) and T5 (SEQ ID NO: 10) were phosphorylated with the aid of a polynucleotide kinase (Roche, Mannheim) following the manufacturer's instructions.

c) Ligation

The ligation of the phosphorylated T1249 DNA fragments with the cut and dephosphorylated vector was accomplished using the T4 DNA ligase (Roche, Mannheim) following the manufacturer's instructions. The transformation of E. coli cells of strain W3110 (ATCC 27325) with the ligation mixture was carried out by electroporation in a manner known to the skilled worker. The transformation mixture was applied to LB/tetracyclin agar plates (10 g/l tryptone, 5 g/l yeast extract, 5 g/l NaCl, 15 g/l agar, 20 mg/l tetracyclin) and incubated overnight at 37° C.

Following plasmid isolation by means of a QIAprep Spin Miniprep Kit (Qiagen, Hilden), the desired transformants were identified by restriction analysis, and the absence of errors was verified by sequence analysis.

In the plasmid pT1249fus which has been obtained in this manner, the T1249 DNA is separated from the hirudin fragment by a DNA sequence which can be cleaved by the protease factor Xa.

Example 3

Construction of pT1249 a) Preparation of the Vector pBaBIFN1

To clone the T1249 DNA, the plasmid vector pBaBIFN1 (which can be isolated from strain DH5α/pBaBIFN1 deposited at the DSMZ (Deutsche Sammlung für Mikroorganismen and Zellkulturen GmbH, D-38142 Brunswick) as DSM 18343, in compliance with the provisions of the Budapest Treaty) was cleaved with the restriction endonucleases BglII and XbaI under the conditions specified by the manufacturer (Roche, Mannheim). The plasmid was subsequently dephosphorylated at the 5' ends by treatment with alkaline phosphatase (Roche, Mannheim) and then purified by means of QIAquick Gel Extraction Kit (Qiagen, Hilden), as in the case of the PCR fragment.

b) Phosphorylation of T1249 DNA Fragments

The nucleic acid sequence for the peptide T1249 was generated synthetically with the aid of oligonucleotides. The oligonucleotides T6 (SEQ ID NO: 11), T7 (SEQ ID NO: 12), T8 (SEQ ID NO: 13), T9 (SEQ ID NO: 14) and T10 (SEQ ID NO: 15) were phosphorylated with the aid of a polynucleotide kinase (Roche, Mannheim) following the manufacturer's instructions.

c) Ligation

The ligation of the phosphorylated T1249 DNA fragments with the cut and dephosphorylated vector was accomplished using the T4 DNA ligase (Roche, Mannheim) following the manufacturer's instructions. The transformation of E. coli cells of strain W3110 (ATCC 27325) with the ligation mixture was carried out by electroporation in a manner known to the skilled worker. The transformation mixture was applied to LB/tetracyclin agar plates (10 g/l tryptone, 5 g/l yeast extract, 5 g/l NaCl, 15 g/l agar, 20 mg/l tetracyclin) and incubated overnight at 37° C.

Figure 3:
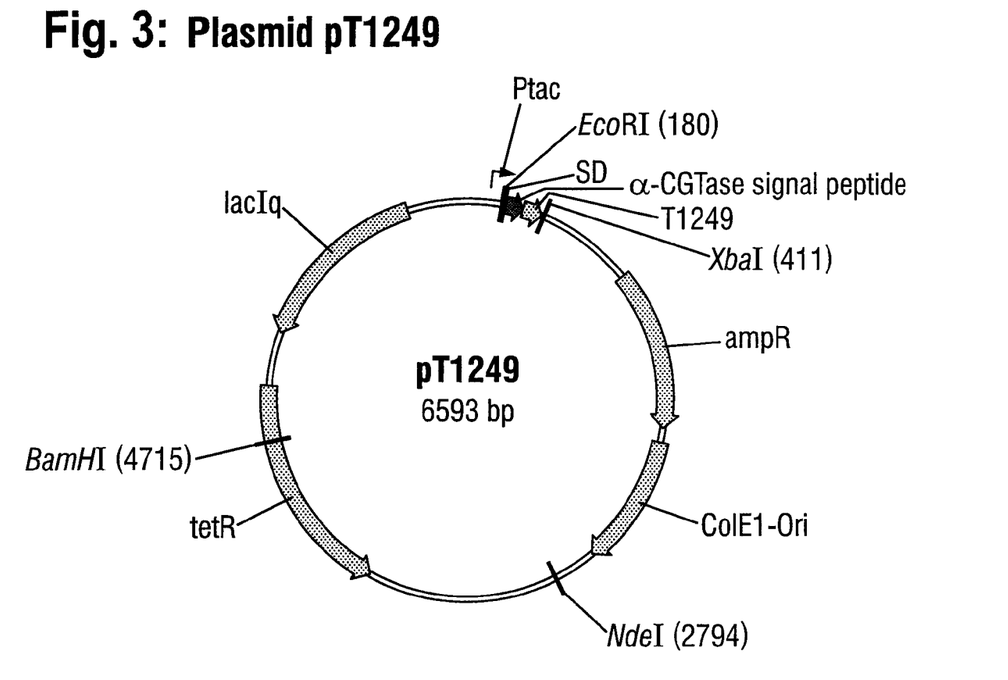
FIG. 3 shows plasmid pT1249

Following plasmid isolation by means of a QIAprep Spin Miniprep Kit (Qiagen, Hilden), the desired transformants were identified by restriction analysis, and the absence of errors was verified by sequence analysis. A plasmid map of plasmid pT1249 is shown in FIG. 3.

Example 4

Construction of a Spy-T1249 Fusion a) Amplification of the Spy Gene

The spy gene was amplified by means of the polymerase chain reaction (PCR) using the Taq DNA polymerase (Roche, Mannheim) and proceeding in the customary manner, which is known to the skilled worker. The template used was plasmid pKP689. The primers used were the oligonucleotides pJF118-seqfw (SEQ ID NO: 16) with the sequence 5'-CAT CGG CTC GTA TAA TGT GTG G-3' and spy-T1249fus (SEQ ID NO: 17) with the sequence 5'-CAA CGA CCT TCG ATA GTA CTT TCA GCA GTT GCA GGC ATT TTA CC-3'.

The DNA fragment obtained in the PCR, which is approximately 586 base pairs in length, was subsequently purified by means of a DNA adsorption column from the QIAprep Spin Miniprep Kit (Qiagen, Hilden) following the manufacturer's instructions.

b) Amplification of the T1249 Gene

The T1249 gene was amplified by means of the polymerase chain reaction (PCR) using the Taq DNA polymerase (Roche, Mannheim) and proceeding in the customary manner, which is known to the skilled worker. The template used was plasmid pT1249fus. The primers used were the oligonucleotides T1249-fus2 (SEQ ID NO: 18) with the sequence 5'-AGT ACT ATC GAA GGT CGT TGG CAG GAA TG-3' and T1249-BfrI (SEQ ID NO: 19) with the sequence 5'-TAG ACC GCT TAA GTC AGA ACC ATT CCC ACA GGC-3'.

The DNA fragment obtained in the PCR, which is approximately 151 base pairs in length, was subsequently purified by means of a DNA adsorption column from the QIAprep Spin Miniprep Kit (Qiagen, Hilden) following the manufacturer's instructions.

c) Fusion of the Spy Gene and the T1249 Gene

The genes spy and T1249 were amplified by means of the polymerase chain reaction (PCR) using the Taq DNA polymerase (Roche, Mannheim) and proceeding in the customary manner, which is known to the skilled worker. The templates were the purified PCR fragments from 4a and 4b (see above), which were employed simultaneously. The primers used were the oligonucleotides pJF118-seqfw (SEQ ID NO: 16) with the sequence 5'-CAT CGG CTC GTA TAA TGT GTG G-3' and T1249-BfrI (SEQ ID NO: 19) with the sequence 5'-TAG ACC GCT TAA GTC AGA ACC ATT CCC ACA GGC-3'.

The DNA fragment obtained in the PCR, which is approximately 717 base pairs in length, was subsequently purified by means of a DNA adsorption column from the QIAprep Spin Miniprep Kit (Qiagen, Hilden) following the manufacturer's instructions.

d) Cloning of the Spy-T1249 Fusion into the Plasmid Vector pKP689

The purified PCR fragment of Example 4c (see above) was cut with the restriction endonucleases EcoRI (Roche, Mannheim) and BfrI (Roche, Mannheim) under the conditions specified by the manufacturer, separated via an agarose gel and then isolated by means of the QIAquick Gel Extraction Kit (Qiagen, Hilden) from the agarose gel following the manufacturer's instructions.

To clone the spy-T1249 fusion, the vector pKP689 was cut with the restriction endonucleases EcoRI and BfrI under the conditions specified by the manufacturer (Roche, Mannheim). The larger portion of the plasmid (approx. 6053 base pairs) was separated from the remainder of the plasmid via an agarose gel and then isolated from the agarose gel by means of the QIAquick Gel Extraction Kit (Qiagen, Hilden) following the manufacturer's instructions.

The DNA fragment was subsequently dephosphorylated at the 5'-ends by treatment with alkaline phosphatase (Roche, Mannheim) and then purified by means of the QIAquick Gel Extraction Kit (Qiagen, Hilden) as in the case of the PCR fragment. The ligation of the PCR fragment with the cut and dephosphorylated DNA fragment was accomplished using the T4 DNA ligase (Roche Mannheim) following the manufacturer's instructions. The transformation of *E. coli* cells of strain W3110 (ATCC 27325) with the ligation mixture was carried out by electroporation in a manner known to the skilled worker. The transformation mixture was applied to LB/tetracyclin agar plates (10 g/l tryptone, 5 g/l yeast extract, 5 g/l NaCl, 15 g/l agar, 20 mg/l tetracyclin) and incubated overnight at 37° C.

Following plasmid isolation by means of a QIAprep Spin Miniprep Kit (Qiagen, Hilden), the desired transformants were identified by restriction analysis, and the absence of errors was verified by sequence analysis.

Figure 4:
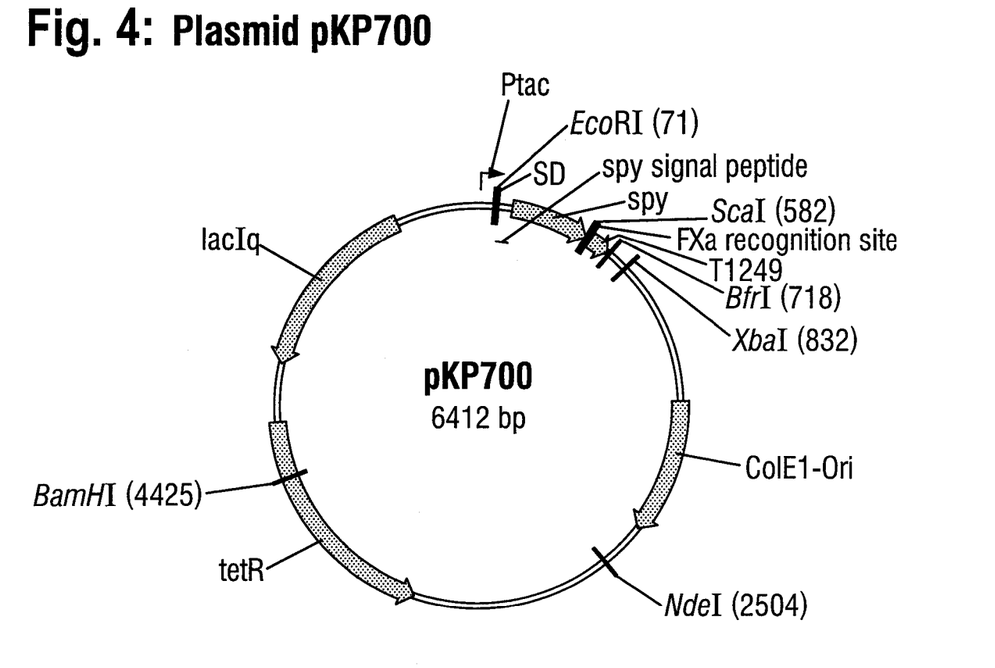
FIG. 4 shows plasmid pKP700

In the plasmid pKP700 (FIG. 4) which has been obtained in this manner, the spy-T1249 fusion is under the control of the inducible tac promoter.

Example 5

Secretion of the Unmodified T1249 Peptide into the Culture Supernatant

The secretion of the Spy-T1249 fusion protein into the culture supernatant was compared with the secretion of the unmodified T1249 peptide into the culture supernatant. To this end, the two strains WCM105/pKP700 and WCM105/pT1249 were grown at 30° C. in 10 ml LB medium in a 100-ml Erlenmeyer flask with 10 g/l of glucose. The *E. coli* strain WCM105 can be obtained as described in EP0338410B1.

At $OD_{600}$=0.5, the production of T1249, and of the fusion protein, respectively, was induced by addition of isopropylthiogalactoside (0.5 mM). After 24 h, 48 h and 72 h, the amount of T1249 and fusion protein, respectively, which had been formed and secreted was investigated in the culture supernatant by separation of the proteins or peptides in SDS gel and detection my means of Coomassie staining.

Figure 6:
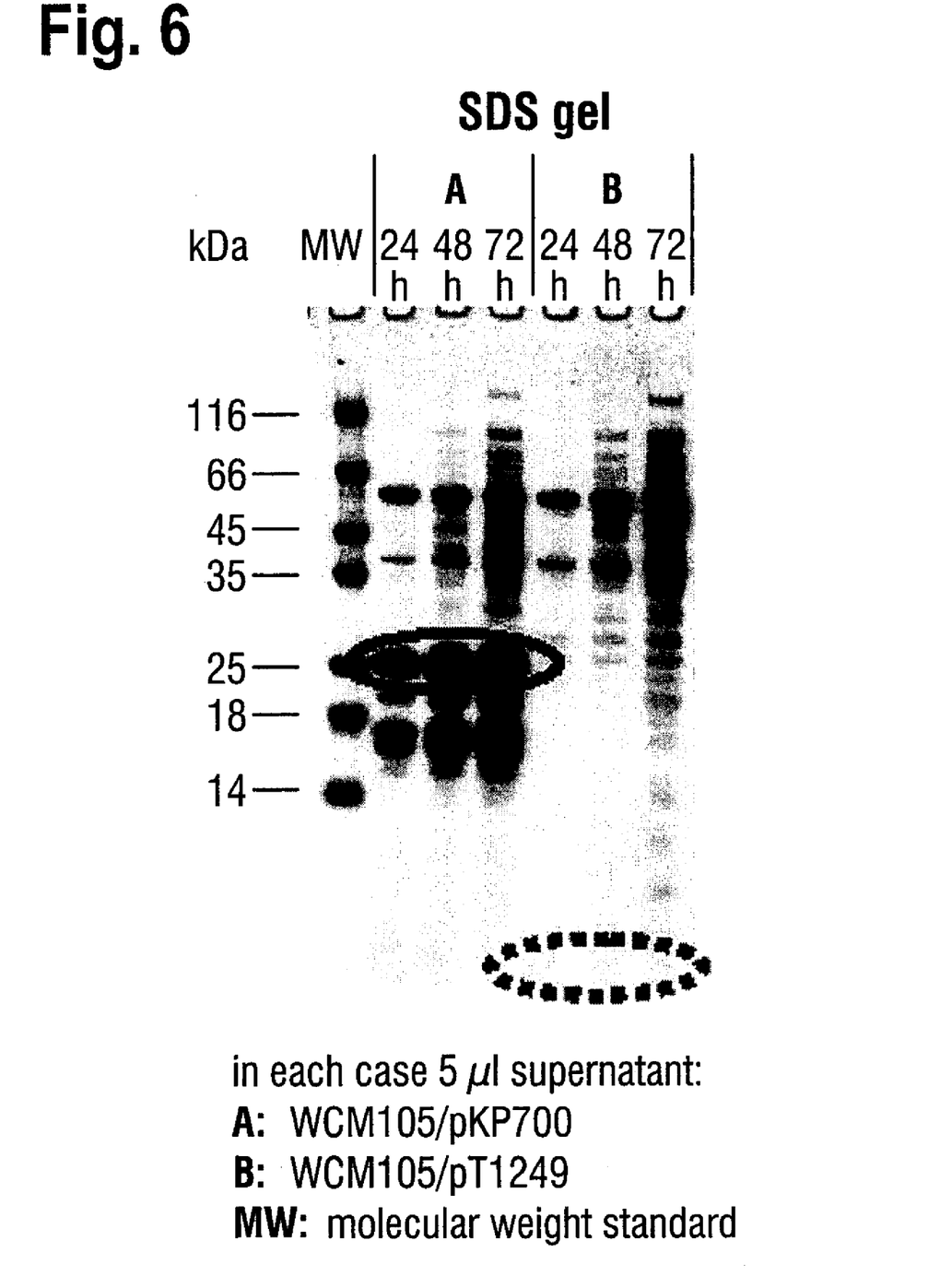
FIG. 6 shows the Coomassie-stained SDS gel from Example 5

The result is shown in FIG. 6. It can be seen clearly that the Spy-T1249 fusion protein is accumulated in the culture supernatant (see oval mark in the gel). The Spy peptide is not accumulated in the culture supernatant (see broken oval mark in the gel).

Example 6

Production of the Unmodified T1249 Peptide

The production of the unmodified T1249 peptide was studied in strains WCM105/pT1249 and WCM105/pKP700. To this end, the two strains were grown at 30° C. in 10 ml LB medium in a 100-ml Erlenmeyer flask with 10 g/l of glucose.

At $OD_{600}$=0.5, the production of the unmodified T1249 peptide was induced by addition of isopropylthiogalactoside (0.5 mM). After 24 h, 48 h and 72 h, the amount of unmodified T1249 peptide formed was detected in the culture supernatant by means of the AQUA method (Gerber et al., 2003, PNAS 100, 6940-6945; Hochleitner et al., 2005, J. Biol. Chem. 280, 2536-2542).

Three reference peptides (SEQ ID NO: 22, SEQ ID NO: 23 and SEQ ID NO: 24) which correspond to tryptic cleavage products of this peptide were selected from the sequence of the unmodified T1249 peptide. These peptides were synthesized, and the absolute quantity was determined by weighing. Thereafter, the reference peptides were derivatized with the deuterated version of acetyl-N-oxysuccinimide ($D_3$-acetyl-N-oxysuccinimide).

The fermentor supernatant was denatured with 6 M guanidinium hydrochloride, reduced (DTT) and alkylated (iodoacetamide) and then digested with trypsin. The digest was derivatized with acetyl-N-oxysuccinimide. Defined amounts of the reference peptides were added, and the digest was then separated by HPLC. Collected fractions were studied by mass spectrometry. Isotope pairs of the reference peptides and the peptides derived from the digest were observed. These isotope pairs differ in mass by 3 daltons. The absolute quantity of the T1249 peptide was determined on the basis of the intensity ratio of the peptide from the digest and of the reference peptide.

When using strain WCM105/pKP700, a factor Xa digest was carried out before the detection via the AQUA method in order to separate the unmodified T1249 peptide from the carrier protein. A 50 μl mixture consisted of 10 μl of 5×buffer (250 mM Tris, pH 8.0; 0.5 M NaCl, 5 mM $CaCl_2$), 15 μl culture supernatant, 1 μl factor Xa (5 μg/μl; Sigma, Taufkirchen, catalog No. F9302) and 24 μl of $H_2O$. The factor Xa digest was performed for 16 h at 22° C.

The quantified yields of unmodified T1249 peptide are listed in Table 1.

TABLE 1

| Strain | Unmodified T1249 peptide [mg/l] | | |
|---|---|---|---|
| | 24 h | 48 h | 72 h |
| WCM105 | 0 | 0 | 0 |
| WCM105/pT1249 | 0 | 21 | 50 |
| WCM105/pKP700 | 4 | 46 | 153 |

Example 7

Construction of a Spy/Interferon α2b Fusion a) Amplification of the Interferon α2b Gene The interferon α2b gene was amplified by means of the polymerase chain reaction (PCR) using the Taq DNA polymerase (Roche, Mannheim) following conventional procedures known to the skilled worker. The template used was plasmid pBaBIFN1 (which can be isolated from DSM 18343). The primers used were the oligonucleotides IFNa2b-fw (SEQ ID NO: 20) with the sequence 5'-P[1]-ACT ATC GAA GGT CGT TGT GAC TTA CCT CAG ACC-3' ([1] oligonucleotide is phosphorylated at the 5'-end) and IFNa2b-rev (SEQ ID NO: 21) with the sequence 5'-ACC TCT TAA GCT ATT ATT CTT TGG AAC GCA AG-3'.

The DNA fragment obtained in the PCR, which is approximately 526 base pairs in length, was subsequently purified by means of a DNA adsorption column from the QIAprep Spin Miniprep Kit (Qiagen, Hilden) following the manufacturer's instructions.

b) Cloning of the Interferon α2b Gene into the Plasmid Vector pKP700

A terminal cleavage site for the restriction endonuclease BfrI was introduced into the PCR fragment via the primer IFNa2b-rev. The purified PCR fragment was cut with the restriction endonuclease BfrI (Roche, Mannheim) under the conditions specified by the manufacturer, separated via an agarose gel and then isolated from the agarose gel by means of the QIAquick Gel Extraction Kit (Qiagen, Hilden) following the manufacturer's instructions.

Figure 5:
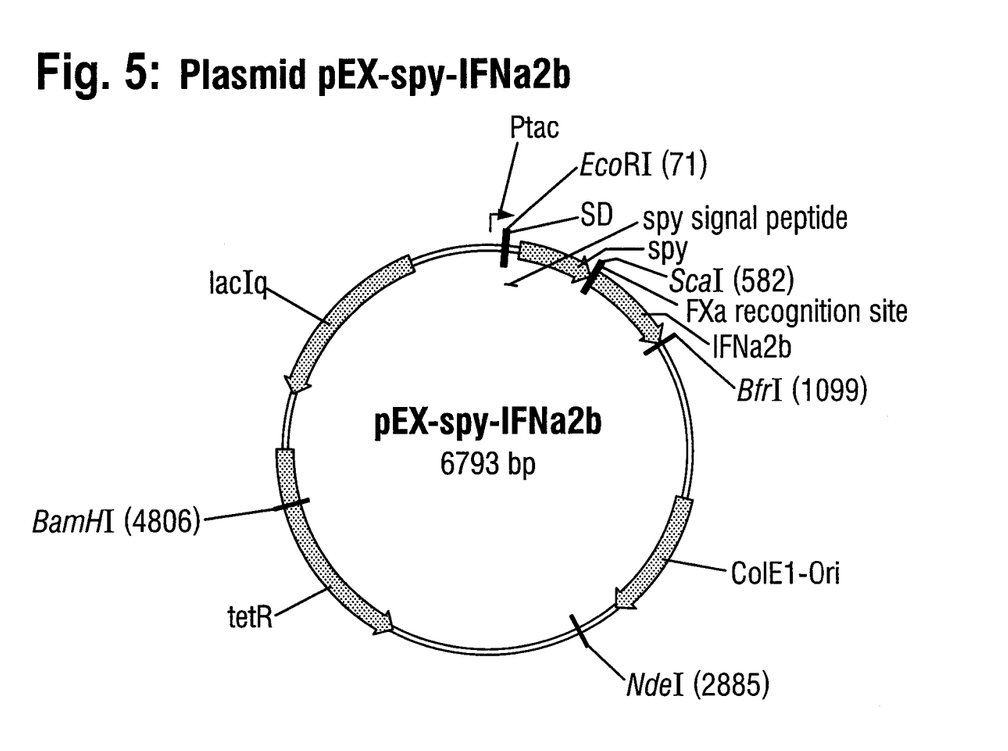
FIG. 5 shows plasmid pEX-spy-IFNa2b

To clone the spy gene, the vector pKP700 was cut with the restriction endonucleases ScaI and BfrI under the conditions specified by the manufacturer (Roche, Mannheim). The plasmid was subsequently dephosphorylated at the 5'-ends by treatment with alkaline phosphatase (Roche, Mannheim) and then purified by means of the QIAquick Gel Extraction Kit (Qiagen, Hilden) as in the case of the PCR fragment. The ligation of the PCR fragment with the cut and dephosphorylated vector was accomplished using the T4 DNA ligase (Roche, Mannheim) following the manufacturer's instructions. The transformation of E. coli cells of strain W3110 (ATCC 27325) with the ligation mixture was carried out by electroporation in a manner known to the skilled worker. The transformation mixture was applied to LB/tetracyclin agar plates (10 g/l tryptone, 5 g/l yeast extract, 5 g/l NaCl, 15 g/l agar, 20 mg/l tetracyclin) and incubated overnight at 37° C. Following plasmid isolation by means of a QIAprep Spin Miniprep Kit (Qiagen, Hilden), the desired transformants were identified by restriction analysis, and the absence of errors was verified by sequence analysis. In the plasmid pEX-spy-IFNa2b (FIG. 5) which has been obtained in this manner, the interferon α2b gene is under the control of the inducible tac promoter.

Example 8

Production of Interferon α2b

The production of interferon α2b in the resulting strains was studied. To this end, the strains were grown at 30° C. in 10 ml of LB medium in a 100 ml Erlenmeyer flask with 10 g/l glucose. At $OD_{600}$=0.5, the production of interferon α2b is induced by addition of isopropylthiogalactoside (0.5 mM).

After 24 hours, 48 hours and 72 hours, the amount of interferon α2b which had been formed and secreted was detected in the culture supernatants by separation of the proteins in an SDS gel and detection in an immunoblot with anti-interferon-specific antibodies.

When strain WCM105/pEX-spy-IFNa2b was used, a factor Xa digest was carried out before the SDS gel in order to separate the interferon α2b from the carrier protein. A 50 µl mixture consisted of 10 µl of 5×buffer (250 mM Tris, pH 8.0; 0.5 M NaCl, 5 mM $CaCl_2$), 15 µl of culture supernatant, 1 µl of factor Xa (5 µg/µl; Sigma, Taufkirchen, Catalog No. F9302) and 24 µl of $H_2O$. The factor Xa digest was performed for 16 h at 22° C.

In each case 5 µl (strain WCM105/pBaBIFN1) or 16.5 µl (strain WCM105/pEX-spy-IFNa2b) supernatant was treated with sample buffer (2×Tris SDS Sample Buffer (Invitrogen, Karlsruhe): 0.125 M Tris-HCl (pH 6.8); 4% w/v SDS; 20% v/v glycerol; 0.005% v/v bromophenol blue; 5% v/v β-mercaptoethanol). In addition, defined amounts of interferon α2b were also applied to act as a standard. Denaturation of the proteins was performed by heating for 5 min to 100° C., cooling for 2 minutes on ice, followed by centrifugation. The proteins were separated by electrophoresis in a 12% strength NuPAGE® Bis-Tris-Gel (Invitrogen, Karlsruhe) using 1×MES-containing Running Buffer (Invitrogen, Karlsruhe) (electrophoresis parameters: 40 minutes at 200 V). Detection and quantification via an immunoblot were carried out following the protocol hereinbelow:

a) Transfer by the Wet-blot Method

Module: Amersham: Hoefer TE 22 Mini Tank Transfer Unit, Code Number: 80-6204-26.

Membrane: nitrocellulose membrane (Schleicher & Schuell; BA 85; cellulose nitrate (E); pore size 0.45 µm). Whatman filters and nitrocellulose membrane were cut into suitable sizes and, together with foam segments (sponges), soaked in transfer buffer (Invitrogen, Karlsruhe) while avoiding air bubbles.

Construction of the sandwich: black panel; joined to cathode; 2 sponges, each 3 mm thick; Whatman paper; SDS polyacrylamide gel; nitrocellulose membrane; Whatman paper; 1 sponge, 6 mm thick; white panel; joined to anode.

Transfer conditions: I=200 mA constant current, U=unlimited, running time=60 minutes.

b) Prehybridization

Incubate membrane in 25 ml of prehybridization buffer; swell for 30 minutes at 20° C.

c) Hybridization Antibody 1

Incubate membrane in 25 ml of prehybridization buffer with 0.15 µg/ml (−>3.75 µg) anti-human-IFN-alpha antibody (Pepro Tech EC via Biozol, Eching; catalog number 500-P32A); swell for 90 minutes or overnight at 20° C.

d) Washing

Swell for 10 seconds in 1×PBS at 20° C.; pour away buffer; swell for 2×15 minutes with 1×PBS at 20° C.; pour away buffer.

e) Hybridization Antibody 2

Incubate membrane in 25 ml of prehybridization buffer with 25 µl (dilution 1:1000) goat anti-rabbit IgG horseradish peroxidase conjugate (HRP) (Southern Biotech via Biozol, Eching; catalog number 4050-05); swell for 60 minutes at 20° C.

f) Washing

Swell for 10 seconds in 1×PBS at 20° C.; pour away buffer; swell for 2×15 minutes with 1×PBS at 20° C.; pour away buffer.

g) Detection Via Chemoluminescence

Prepare Lumi-Light Western Blotting Substrate (Roche, Mannheim): mix Lumi-Light Luminol/Enhancer Solution and Lumi-Light Stable Peroxide Solution in the ratio 1:1:3 ml per nitrocellulose membrane.

Incubate blot for 5 minutes at 20° C. with Lumi-Light Western Blotting Substrate, drain excess, cover membrane with cling film and immediately place X-ray film (Kodak, X-OMAT) thereon, expose for 2 minutes, develop and fix. In the case of weak signals, the exposure is repeated over a prolonged period.

h) Buffer

Prehybridization buffers: 5% w/v skim milk powder in 1×PBS; 10×PBS: 100 mM $NaH_2PO_4$; 1.5 M NaCl, pH 7.5 with NaOH, 0.5% Triton 100; 1×PBS: dilute 10×PBS 1:10 in fully demineralized water.

i) Quantification

The blot was evaluated quantitatively after scanning into a Biorad GS-800 Calibrated Densitometer by means of the Quantity One 1-D-Analysis software (Biorad, Munich) by comparison with the standard which had been applied. The quantified interferon α2b yields are listed in Table 2.

TABLE 2

| Strain | Interferon α2b [mg/l] | | |
|---|---|---|---|
| | 24 h | 48 h | 72 h |
| WCM105 | 0 | 0 | 0 |
| WCM105/pBaBIFN1 | 5 | 25 | 145 |
| WCM105/pEX-spy-IFNa2b | 21 | 102 | 410 |

We claim:

1. A DNA construct for producing a target protein in *E. coli*, the DNA construct comprising a nucleic acid sequence encoding a signal peptide which is operably linked with a gene coding for a carrier protein which is linked with a gene coding for the target protein via a gene coding for a cleavable sequence S, wherein the gene coding for a carrier protein is a spy gene from *E. coli* wherein the spy gene comprises SEQ ID NO: 1 or a degenerate variant thereof.

2. The DNA construct of claim 1, wherein the nucleic acid sequence coding for the signal peptide is a nucleic acid encoding for the signal-peptide of the *E. coli* spy gene.

3. The DNA construct of claim 1, wherein the nucleic acid sequence codes for a target protein selected from the group consisting of interferons, interleukins, interleukin receptors, interleukin receptor antagonists, granulocyte-colony-stimulating factors, granulocyte-macrophage-colony-stimulating factors, macrophage-colony-stimulating factors, leukemia inhibitors, stem-cell growth factors, tumor necrosis factors, growth hormones, insulin-like growth factors, fibroblast growth factors, platelet-derived growth factors, transforming growth factors, hepatocyte growth factors, bone-morphogenetic factors, nerve growth factors, brain-derived neurotrophic factors (BDNF), glia-cell-line-derived neurotrophic factors, angiogenesis inhibitors, tissue plasminogen activators, blood clotting factors, trypsin inhibitors, elastase inhibitors, immunoglobulins, single-chain antibodies, complement components, hypoxia-inducing stress proteins, protein kinases, proto-oncogen products, transcription factors, virus-constitutive proteins, proinsulin, prourokinase, erythropoietin, thrombopoietin, neurotrophin, protein C, glucocerebrosidase, superoxide dismutase, renin, lysozyme, P450, prochymosin, lipocortin, reptin, serum albumin, streptokinase, tenecteplase, and CNTF (ciliary neurotrophic factor).

4. The DNA construct of claim 1, wherein the cleavable sequence S is a nucleic acid sequence that allows chemical or enzymatic cleavage of target and carrier protein in the translated fusion protein.

5. The DNA construct of claim 4, wherein the cleavable sequence S allows enzymatic cleavage of the fusion protein.

6. The DNA construct of claim 4, wherein the cleavable sequence S allows cleavage of the fusion protein by proteases.

7. The DNA construct of claim 6, wherein the cleavable sequence S allows cleavage of the target protein by eukaryotic protease factor Xa.

8. A plasmid comprising the DNA construct of claim 1.

9. A method of generating a fusion-protein-secreting microorganism strain, wherein the DNA construct of claim 1 is introduced into a microorganism strain from the family Enterobacteriaceae.

10. A method of generating a fusion-protein-secreting microorganism strain, wherein the plasmid of claim 8 is introduced into a microorganism strain from the family Enterobacteriaceae.

11. A microorganism strain comprising the DNA construct of claim 1.

12. A microorganism strain comprising the plasmid of claim 8.

13. A process for the fermentative production of a fusion protein by a microorganism strain, wherein a microorganism strain as claimed in claim 11 is cultured in a fermentation medium, during which process a fusion comprising a Spy protein, a target protein and a cleavable sequence (S) is formed, and, after the fermentation, the fermentation medium is separated from the cells of the microorganism strain.

14. The process of claim 13, wherein, after the fermentation medium has been separated off, the target protein is isolated from the periplasm of the cells, the carrier protein first being removed chemically or enzymatically from the target protein and the target protein subsequently being purified.

15. The process of claim 13, wherein, after the fermentation medium has been separated off, the target protein is isolated from the fermentation medium, the carrier protein first being removed chemically or enzymatically from the target protein and the target protein subsequently being purified.

* * * * *